(12) United States Patent
Squires et al.

(10) Patent No.: US 10,695,107 B2
(45) Date of Patent: Jun. 30, 2020

(54) SPINAL IMPLANT SYSTEM AND METHODS OF USE

(71) Applicant: Warsaw Orthopedic, Inc., Warsaw, IN (US)

(72) Inventors: Craig M. Squires, Cordova, TN (US); Mark C. Dace, Collierville, TN (US); Nikhil S. Kulkarni, Memphis, TN (US); Chris E. Johnson, Germantown, TN (US); John G. Heller, Atlanta, GA (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

(21) Appl. No.: 14/957,780

(22) Filed: Dec. 3, 2015

(65) Prior Publication Data

US 2017/0156764 A1 Jun. 8, 2017

(51) Int. Cl.
*A61B 17/70* (2006.01)

(52) U.S. Cl.
CPC ...... *A61B 17/7071* (2013.01); *A61B 17/7059* (2013.01)

(58) Field of Classification Search
CPC ............ A61B 17/7071; A61B 17/7067; A61B 17/7059; A61B 17/7083; A61B 17/808
See application file for complete search history.

(56) References Cited

U.S. PATENT DOCUMENTS

| | | | | |
|---|---|---|---|---|
| 3,716,050 A | * | 2/1973 | Johnston | A61B 17/8061 606/286 |
| 4,800,874 A | * | 1/1989 | David | A61B 17/8061 606/286 |
| 5,709,686 A | * | 1/1998 | Talos | A61B 17/8057 606/280 |
| 5,951,557 A | * | 9/1999 | Luter | A61B 17/80 606/286 |
| 6,080,157 A | * | 6/2000 | Cathro | A61B 17/7071 606/279 |
| 6,419,703 B1 | * | 7/2002 | Fallin | A61F 2/4405 606/247 |
| 6,572,617 B1 | * | 6/2003 | Senegas | A61B 17/7071 606/263 |
| 6,660,007 B2 | * | 12/2003 | Khanna | A61B 17/7071 606/280 |
| 8,105,366 B2 | | 1/2012 | Null et al. | |

(Continued)

OTHER PUBLICATIONS

Office Action issued by Japan Patent Office, dated Jul. 30, 2019, Japanese Patent Application No. 2018-184357.

*Primary Examiner* — Jan Christopher L Merene

(57) ABSTRACT

A spinal implant includes an intermediate portion and a first portion extending in a transverse orientation from the intermediate portion. The first portion includes an inner surface connectable with vertebral tissue adjacent a lamina. A second portion is spaced from the first portion and extends in a transverse orientation from the intermediate portion. The second portion includes an inner surface connectable with vertebral tissue adjacent a lamina. At least one of the first portion and the second portion includes an outer surface having a mating element engageable with a mating element of a surgical instrument. Systems, surgical instruments and methods are disclosed.

18 Claims, 12 Drawing Sheets

(56) References Cited

U.S. PATENT DOCUMENTS

| | | | |
|---|---|---|---|
| 8,435,265 B2* | 5/2013 | Konieczynski | A61B 17/7071 606/246 |
| 8,915,946 B2 | 12/2014 | Khanna | |
| 8,926,664 B1* | 1/2015 | Millhouse | A61B 17/7071 606/246 |
| 2002/0143338 A1* | 10/2002 | Orbay | A61B 17/68 606/287 |
| 2003/0125738 A1* | 7/2003 | Khanna | A61B 17/7071 606/279 |
| 2004/0030388 A1* | 2/2004 | Null | A61B 17/7059 623/17.11 |
| 2004/0172040 A1* | 9/2004 | Heggeness | A61B 17/8004 606/105 |
| 2005/0043740 A1* | 2/2005 | Haid, Jr. | A61B 17/025 606/90 |
| 2005/0131412 A1* | 6/2005 | Olevsky | A61B 17/808 606/86 B |
| 2005/0234454 A1* | 10/2005 | Chin | A61B 17/7007 606/287 |
| 2005/0273100 A1* | 12/2005 | Taylor | A61B 17/7035 623/17.11 |
| 2006/0025771 A1* | 2/2006 | Jackson | A61B 17/7032 74/1 R |
| 2007/0083203 A1* | 4/2007 | Ribeiro | A61B 17/1604 606/279 |
| 2007/0225806 A1 | 9/2007 | Squires et al. | |
| 2008/0215096 A1* | 9/2008 | Nash | A61B 17/8042 606/249 |
| 2009/0177239 A1* | 7/2009 | Castro | A61B 17/1728 606/86 B |
| 2009/0318968 A1 | 12/2009 | Duggal et al. | |
| 2010/0057127 A1* | 3/2010 | McGuire | A61B 17/7071 606/246 |
| 2010/0069960 A1* | 3/2010 | Chaput | A61B 17/7071 606/249 |
| 2010/0185240 A1* | 7/2010 | Mangione | A61B 17/7071 606/250 |
| 2011/0106083 A1* | 5/2011 | Voellmicke | A61B 17/7071 606/70 |
| 2011/0106087 A1* | 5/2011 | Gamache | A61B 17/7071 606/71 |
| 2011/0106169 A1* | 5/2011 | Zalenski | A61B 17/7071 606/279 |
| 2011/0125269 A1 | 5/2011 | Moskowitz et al. | |
| 2011/0270397 A1 | 11/2011 | Mac-Thiong | |
| 2012/0071931 A1* | 3/2012 | Perez-Cruet | A61B 17/7071 606/279 |
| 2012/0165942 A1* | 6/2012 | Khanna | A61B 17/7071 623/17.16 |
| 2012/0271359 A1* | 10/2012 | Stevenson | A61B 17/7071 606/281 |
| 2012/0316647 A1* | 12/2012 | Farin | A61B 17/8858 623/17.13 |
| 2013/0060283 A1* | 3/2013 | Suh | A61B 17/7071 606/246 |
| 2013/0123793 A1* | 5/2013 | Kehres | A61B 17/00 606/104 |
| 2013/0197641 A1* | 8/2013 | Shepard | A61B 17/7071 623/17.11 |
| 2013/0211524 A1 | 8/2013 | Hugues | |
| 2014/0088648 A1* | 3/2014 | Chind | A61B 17/7071 606/251 |
| 2014/0114361 A1* | 4/2014 | Robinson | A61B 17/7071 606/281 |
| 2015/0257789 A1* | 9/2015 | Squires | A61B 17/70 606/246 |
| 2015/0257795 A1* | 9/2015 | Squires | A61F 2/4405 606/246 |
| 2015/0265317 A1* | 9/2015 | Ricica | A61B 17/7071 606/280 |
| 2016/0113770 A1* | 4/2016 | Early | A61B 17/8095 623/23.39 |
| 2016/0135854 A1* | 5/2016 | Khanna | A61B 17/7071 606/298 |

* cited by examiner

SPINAL IMPLANT SYSTEM AND METHODS OF USE

TECHNICAL FIELD

The present disclosure generally relates to spinal implants for the treatment of musculoskeletal disorders, and more particularly to a spinal implant system that includes a spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column.

Non-surgical treatments, such as medication, rehabilitation and exercise can be effective, however, may fail to relieve the symptoms associated with these disorders. Surgical treatment of these spinal disorders includes fusion, fixation, discectomy, laminectomy, laminoplasty and implantable prosthetics. For example, laminoplasty treatments may employ implants, which may include plates and bone fasteners to stabilize vertebrae and facilitate healing. This disclosure describes an improvement over these prior technologies.

SUMMARY

In one embodiment, a spinal implant is provided. The spinal implant includes an intermediate portion and a first portion extending in a transverse orientation from the intermediate portion. The first portion includes an inner surface connectable with vertebral tissue adjacent a lamina. A second portion is spaced from the first portion and extends in a transverse orientation from the intermediate portion. The second portion includes an inner surface connectable with vertebral tissue adjacent a lamina. At least one of the first portion and the second portion includes an outer surface having a mating element engageable with a mating element of a surgical instrument. In some embodiments, systems, surgical instruments and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
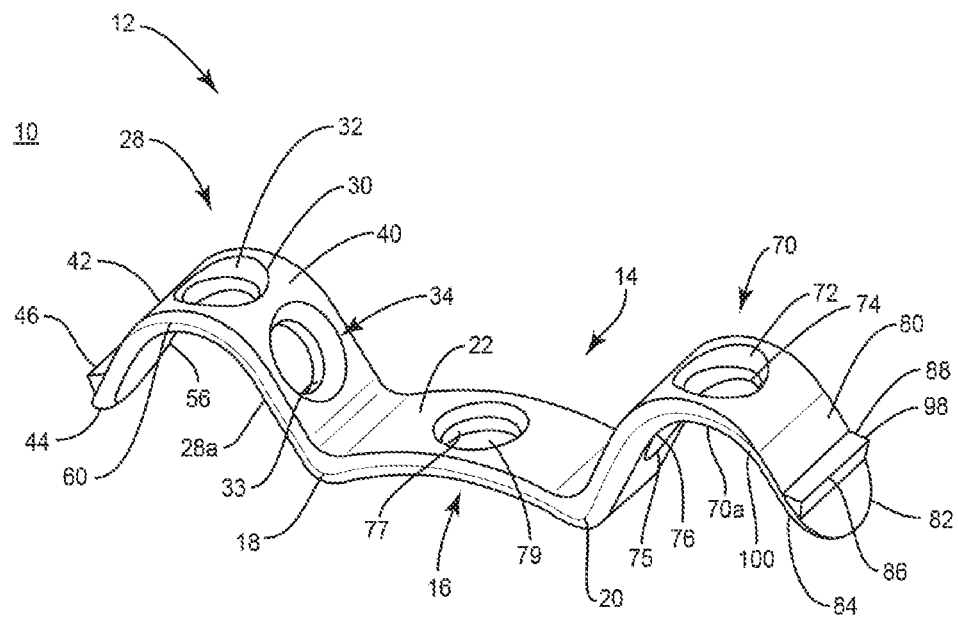
FIG. 1 is a perspective view of components of one embodiment of a system in accordance with the principles of the present disclosure.

The exemplary embodiments of the spinal implant system and related methods of use disclosed are discussed in terms of medical devices for the treatment of musculoskeletal disorders and more particularly, in terms of a spinal implant system that includes a spinal implant and a method for treating a spine. In some embodiments, the systems and methods of the present disclosure are employed with a laminoplasty procedure. In some embodiments, the present disclosure provides a spinal implant system employed with a laminoplasty surgical technique that includes removing a portion of vertebral tissue, such as, for example, a portion of a spinous process and/or lamina and placing an implant adjacent and/or between the tissue adjacent a vertebra to form a bridge. In some embodiments, the spinal implant includes a plate. In some embodiments, the spinal implant includes a gullwing shaped plate.

In some embodiments, the spinal implant system comprises a spinal implant that includes a laminoplasty plate. In some embodiments, the spinal implant system comprises a spinal implant that includes a french-door style laminoplasty implant. In some embodiments, the spinal implant system is employed with a method comprising a french door style laminoplasty. In some embodiments, the spinal implant system is employed with a method comprising a laminoplasty and includes a plate having material, such as, for example, hydroxyapatite (HA) and/or a bone strut, disposed between divided laminae to secure the laminae in an opened position.

In some embodiments, the spinal implant system comprises a spinal implant that includes a plate having a curved cross-section to be consistent with natural anatomy and central arms, which provide stops for maintaining desired spacing between divided ends of laminae. In some embodiments, the spinal implant includes a plate having a roughened surface that mates against bone to provide stability during insertion. In some embodiments, the spinal implant includes a plate having a roughened surface for fixation to bone once crimped and/or screwed into final position. In some embodiments, the spinal implant includes a plate having additional surface area for bony integration. In some embodiments, the spinal implant includes a plate having teeth and/or rails located on bone mating surfaces to provide fixation to bone once crimped and/or screwed into final position. In some embodiments, the spinal implant includes a plate having screw holes for attachment to bone. In some embodiments, the spinal implant includes a plate having screw holes oriented transverse to laminae and oriented such that a screw may be placed along an axis of the laminae. In some embodiments, the spinal implant includes a plate having a mating element, such as, for example, a post, loop, ridge and/or hole for alignment/attachment with a mating element of a surgical instrument.

In some embodiments, the spinal implant system comprises a spinal implant that includes a plate that connects to tissue surrounding the laminae, such as, for example, lateral mass and/or adjacent musculature. In some embodiments, the plate can be manipulated and selectively fit to anatomy, such as, for example, the plate can be made from titanium thin enough to be bent to match the shape of a spinous process/laminae. In some embodiments, the spinal implant system includes an insertion instrument that includes a dovetail portion configured for mating with a dovetail opening of a spinal implant. In some embodiments, the insertion instrument includes an opening configured for disposal of a surgical instrument, such as, for example, a drill, tap, and/or a screw driver. In some embodiments, the spinal implant system comprises one or more screws with a male driving feature and a surgical instrument with a corresponding female feature for holding, and driving the screws.

In some embodiments, the spinal implant system comprises a spinal implant that includes a plate having a gripping element disposed on an outside surface thereof that provides a gripping capability for a surgical instrument to crimp the plate onto mating bone. In some embodiments, this configuration provides for crimping of the plate with bone by the surgical instrument to maintain a firm, non-slip grip of the plate by the surgical instrument. In some embodiments, this configuration provides increased protection due to the close proximity to a spinal cord. In some embodiments, the spinal implant system comprises screws employed with the plate and including mating surfaces that mate with a mating surface in screw holes of the plate. In some embodiments, the spinal implant system comprises screws having an external feature that is designed to mate with a corresponding internal feature on a screw driving instrument. In some embodiments, this configuration prevents a head of the screw from becoming deformed as a result of engagement with the driver, which permits improved retention of the screw by the driver. In some embodiments, this configuration reduces accidental disengagement from the driver during a surgical procedure.

In some embodiments, the spinal implant system comprises one or more trials. In some embodiments, the trials are dual-ended for trialing a plurality of alternately configured and/or dimensioned implants. In some embodiments, the trials include a handle that is tapered to indicate whether an end is larger/smaller. In some embodiments, the trials can be made from titanium and anodized for color coding to provide visual indicia of a selected configuration and/or dimension of an implant. For example, a green trial provides visual indicia of a gullwing shaped plate.

In some embodiments, the spinal implant system is employed with a french-door style cervical laminoplasty plate. In some embodiments, the spinal implant system includes an instrument. In some embodiments, the instrument includes one or more tips that can be transversely oriented, curved or linear. In some embodiments, the instrument includes one or more tips having mating elements, such as, for example, teeth, for engaging, gripping and/or crimping a spinal implant, as described herein.

In some embodiments, the spinal implant system includes an implant having a curved section adjacent an intermediate portion thereof and configured to be contoured with a patient's natural anatomy, such as, for example, a spinal canal. In some embodiments, the spinal implant system includes a spinal implant having a roughened surface configured to mate with bone to provide stability during insertion. In some embodiments, the spinal implant includes additional surface area for bony integration. In some embodiments, the spinal implant is provided that includes a screw hole configured to receive a screw for attachment to bone.

In some embodiments, the spinal implant includes plate material configured for manipulation such that the spinal implant can be fit to a patient's anatomy. In some embodiments, the spinal implant includes a material, such as, for example, a titanium sheet that is bent to match a shape of a spinous process and/or a lamina. In some embodiments, a spinal implant is provided that maintains space between vertebral tissue where tissue is removed and is configured to receive a graft or scaffold. In some embodiments, the spinal implant includes a portion for receiving the graft or scaffold to facilitate bone growth.

In some embodiments, the present disclosure may be employed to treat spinal disorders such as, for example, degenerative disc disease, disc herniation, osteoporosis, spondylolisthesis, stenosis, tumor and fractures. In some embodiments, the present disclosure may be employed with other osteal and bone related applications, including those associated with diagnostics and therapeutics. In some embodiments, the disclosed systems and methods may be alternatively employed in a surgical treatment with a patient in a prone or supine position, and/or employ various surgical approaches to the spine, including posterior, posterior midline, medial, lateral, postero-lateral approaches, and in other body regions. The systems and methods of the present disclosure may also be alternatively employed with procedures for treating the lumbar, cervical, thoracic and pelvic regions of a spinal column. The systems and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, outer, inner, terminal (denoting position or location), left and right, posterior, anterior, and the like, are for illustrative purposes only and can be varied within the scope of the disclosure. For example, the references "superior" and "inferior" are relative and used only in the context to the other, and are not necessarily "upper" and "lower".

As used in the specification and including the appended claims, "treating" or "treatment" of a disease or condition refers to performing a procedure that may include administering one or more drugs to a patient in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (for example, preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, for example, arresting its development, or relieving the disease, for example, causing regression of the disease. For example, treatment can include reducing acute or chronic inflammation; alleviating pain and mitigating and inducing re-growth of new ligament, bone and other tissues; as an adjunct in surgery; and/or any repair procedure. As used in the specification and including the appended claims, the term "tissue" includes soft tissue, ligaments, tendons, cartilage and/or bone unless specifically referred to otherwise.

Figure 2:
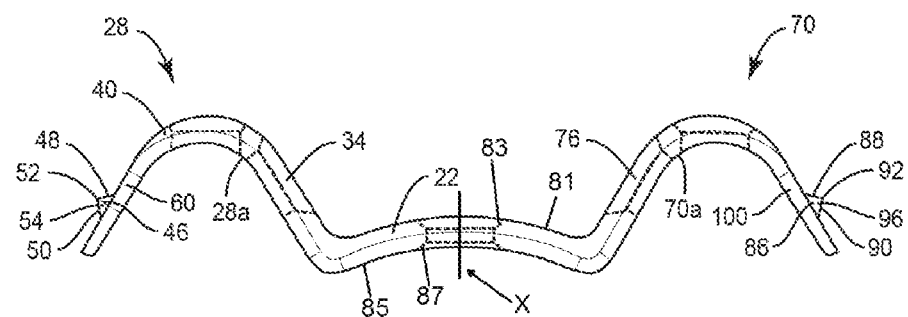
FIG. 2 is a side view of the components shown in FIG. 1.

The following discussion includes a description of a spinal implant system and related methods of employing the spinal implant system in accordance with the principles of the present disclosure. Alternate embodiments are also disclosed. Reference is made in detail to the exemplary embodiments of the present disclosure, some of which are illustrated in the accompanying figures. Turning to FIGS. 1-2, there are illustrated components of a spinal implant system 10 including a spinal implant in accordance with the principles of the present disclosure.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, superelastic metallic alloys (e.g., Nitinol, super elasto-plastic metals, such as GUM METAL®), ceramics and composites thereof such as calcium phosphate (e.g., SKELITE™), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate such as HA, corraline HA, biphasic calcium phosphate, tricalcium phosphate, or fluorapatite, tricalcium phosphate (TCP), HA-TCP, calcium sulfate, or other resorbable polymers such as polyaetide, polyglycolide, polytyrosine carbonate, polycaroplaetohe and their combinations, biocompatible ceramics, mineralized collagen, bioactive glasses, porous metals, bone particles, bone fibers, morselized bone chips, bone morphogenetic proteins (BMP), such as BMP-2, BMP-4, BMP-7, rhBMP-2, or rhBMP-7, demineralized bone matrix (DBM), transforming growth factors (TGF, e.g., TGF-β), osteoblast cells, growth and differentiation factor (GDF), insulin-like growth factor 1, platelet-derived growth factor, fibroblast growth factor, or any combination thereof.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials.

Spinal implant system 10 can be employed, for example, in laminoplasty procedures to treat patients suffering from a spinal disorder to provide stabilization and decompression. The components of spinal implant system 10 may be monolithically formed, integrally connected or include fastening elements and/or instruments, for example, as described herein.

Spinal implant system 10 includes a spinal implant 12 configured for disposal with vertebral tissue in a laminoplasty procedure to treat patients suffering from a spinal disorder to provide stabilization and decompression. In some embodiments, spinal implant 12 is configured for stabilizing vertebral tissue, such as, for example, divided and/or separated lamina, transverse process, pars interarticularis, facet or spinous process portions of one or more vertebral levels, as shown and described for example with regard to FIGS. 15 and 16. In some embodiments, spinal implant 12 is configured for stabilizing one or more vertebral levels via attachment with a vertebral level having removed, non-separated portions of vertebral tissue, such as, for example, a lamina, transverse process, pars interarticularis, facet or spinous process, for example, such that a cavity is created in the vertebral tissue, however, the tissue is not separated and spaced apart, as shown and described for example with regard to FIG. 13.

Spinal implant 12 includes a plate 14 having a tissue barrier 16. Tissue barrier 16 extends between an end 18 and an end 20, and includes a portion 22 disposed intermediate and/or therebetween. Tissue barrier 16 includes a wall having a substantially uniform, rectangular cross section. In some embodiments, tissue barrier 16 can have alternate configurations, such as, tubular, oval, oblong, irregular, undulating, non-uniform, variable, hollow, wire, mesh and/or tapered.

End 18 is spaced apart from end 20, and portion 22 has a non-planar face, such as, for example, an arcuate configuration including a curvature that is oriented adjacent tissue, such as, for example, a spinal canal. In some embodiments, portion 22 can face and/or engage adjacent, opposing, and/or distributed locations of vertebral tissue, as described herein, of a posterior, posterior mid-line, medial, lateral and/or postero-lateral portion of vertebrae. In some embodiments, portion 22 can comprise alternate configurations, such as, for example, concave, linear or angled.

End 18 includes a portion, such as, for example, a transverse extension 28 that extends from portion 22 at an angular orientation. In some embodiments, extension 28 includes an undulating configuration, which comprises at least a portion of a gullwing configuration of spinal implant 12, as shown in FIG. 1. In some embodiments, the undulating configuration of extension 28 and/or the gullwing configuration of spinal implant 12 facilitates manipulation thereof for engagement with anatomy, as described herein.

Extension 28 includes a fixation surface, such as, for example, surface 28a oriented to face and/or engage vertebral tissue, such as, for example, a lamina. In some embodiments, all or only a portion of extension 28 is engageable with a cut surface of tissue, as described herein. In some embodiments, surface 28a is roughened to facilitate engagement with tissue and provides an initial provisional fixation with tissue. In some embodiments, surface 28a includes teeth and/or rails to facilitate fixation with tissue. In some embodiments, surface 28a is smooth, porous, textured, rough, semi-porous, dimpled and/or polished.

In some embodiments, extension 28 can comprise a portion of spinal implant 12 that abuts and/or engages a separated surface of an anterior facing portion of vertebral tissue, as described herein. In some embodiments, extension 28 can extend from portion 22 at various angular orientations, such as, for example, acute, obtuse and in a range of 0-360 degrees. In some embodiments, extension 28 can extend from portion 22 in a perpendicular, transverse, substantially aligned, twisted or helical orientation.

Figure 5:
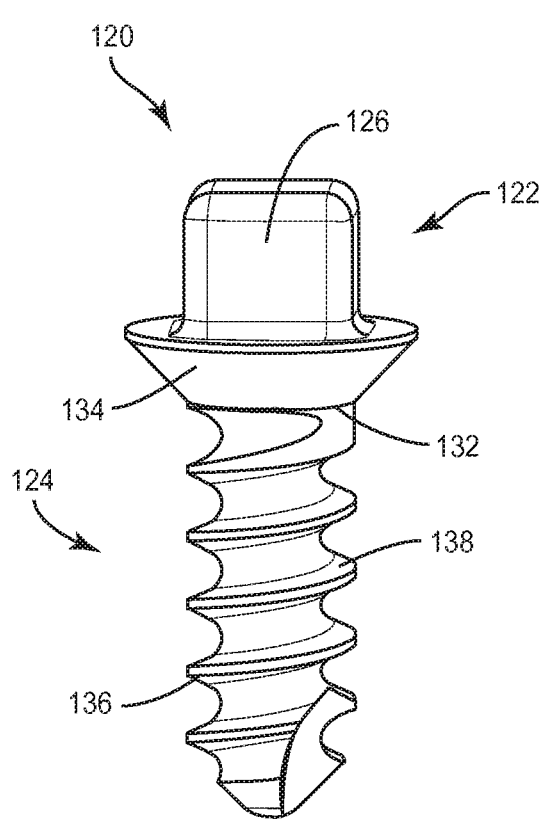
FIG. 5 is a perspective view of components of one embodiment of a system in accordance with the principles of the present disclosure.
Figure 6:
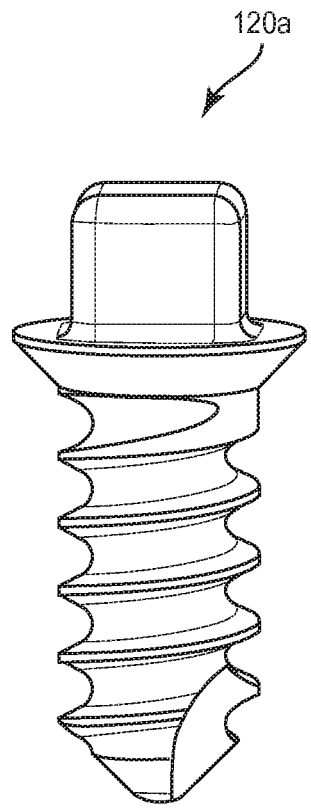
FIG. 6 is a perspective view of components of one embodiment of a system in accordance with the principles of the present disclosure.

Extension 28 includes an inner surface 30 that defines a cavity, such as, for example, an opening 32 configured to receive a bone fastener, such as, for example, a bone screw 120, as discussed herein and shown in FIGS. 5 and 6. Extension 28 includes an inner surface 33 that defines a cavity, such as, for example, an opening 34 configured to receive a bone screw 120. Bone screw 120 attaches extension 28 and spinal implant 12 with vertebral tissue, as described herein. In some embodiments, extension 28 may include one or a plurality of cavities configured for disposal of a bone fastener.

Figure 3:
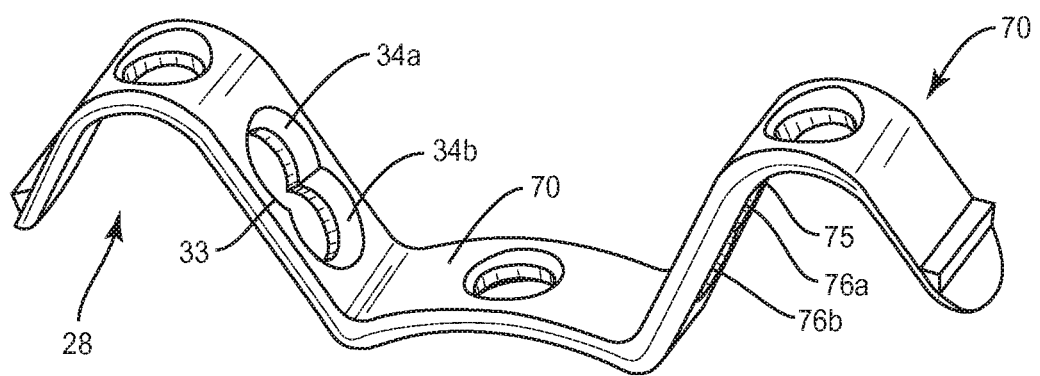
FIG. 3 is a perspective view of components of one embodiment of a system in accordance with the principles of the present disclosure.
Figure 4:
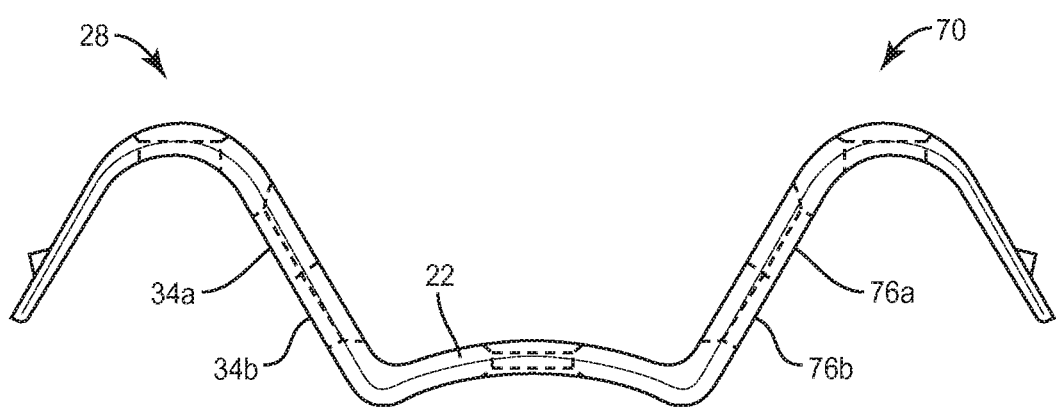
FIG. 4 is a side view of the components shown in FIG. 3.

In some embodiments, inner surface 33 defines an elongated cavity, which includes openings 34a, 34b to selectively orient bone screw 120 for penetrating vertebral tissue, as shown in FIGS. 3 and 4. In some embodiments, openings 34a, 34b communicate and are overlapping to provide adjustability of bone screw 120 for selectively orienting bone screw 120 for penetrating vertebral tissue. In some embodiments, openings 34a, 34b are spaced and do not overlap to provide adjustability of bone screw 120 for selectively orienting bone screw 120 for penetrating vertebral tissue. In some embodiments, the elongated cavity includes a circular opening 34a that defines a center axis and a circular opening 34b that defines a center axis. In some embodiments, the elongated cavity can include one or a plurality of openings, which may be disposed in linear alignment, series, an arc, undulating, offset, staggered, uniform, non-uniform, angled, cluster, random and/or cloverleaf configuration. In some embodiments, the center axes are relatively disposed in a parallel or transverse orientation. In some embodiments, openings 34a, 34b comprise a figure eight configuration such that opening 34a communicates with opening 34b to provide adjustability of bone screw 120 to selectively orient bone screw 120 for penetrating vertebral tissue. In some embodiments, an opening may have alternate configurations, such as, for example, oval, oblong, triangular, square, hexagonal, polygonal, irregular, uniform, non-uniform and/or tapered. In some embodiments, opening 32 and/or opening 34 is configured to orient bone screw 120 along a transverse axis of the lamina. In some embodiments, opening 32 and/or opening 34 is configured to orient bone screw 120 along a longitudinal axis of the lamina.

In some embodiments, spinal implant system 10 includes one or more fasteners that may be engaged with vertebral tissue in various orientations, such as, for example, series, parallel, offset, staggered and/or alternate vertebral levels. In some embodiments, the fasteners may comprise pedicle screws, mono-axial screws, uni-planar screws, facet screws, fixed screws, tissue penetrating screws, conventional screws, expanding screws, wedges, anchors, buttons, clips, snaps, friction fittings, compressive fittings, expanding rivets, staples, nails, adhesives, posts, fixation plates and/or posts.

Extension 28 includes an outer surface 40, as shown in FIGS. 1 and 2. Outer surface 40 extends between an end 42 and an end 44. Outer surface 40 includes a mating element, such as, for example, a ridge 46. Ridge 46 is configured for engagement with a surgical instrument, such as, for example, a surgical delivery instrument I, as described herein. Ridge 46 includes a surface, such as, for example, a ramp 48 and a surface, such as, for example, a ramp 50. Ramps 48, 50 are oriented to define an apex 52. Ramp 48, ramp 50 and/or apex 52 are configured as a grip surface to resist and/or prevent surgical delivery instrument I from disengagement and/or slipping from spinal implant 12 to resist and/or prevent undesired engagement and/or damage to adjacent tissue.

Ramps 48, 50 define end surfaces 54, 56. Surfaces 54, 56 are configured to facilitate alignment and engagement of surgical delivery instrument I with spinal implant 12, as described herein. In some embodiments, ridge 46 extends in a transverse orientation relative to ends 42, 44. In some embodiments, ridge 46 extends a selected distance between ends 42, 44. In some embodiments, the mating element includes a tooth disposed transversely along surface 40. In some embodiments, the mating element includes a plurality of teeth. In some embodiments, one or more teeth may have various configurations, for example, parallel, converging, diverging, irregular, tapered, offset, staggered, uniform and non-uniform. In some embodiments, the teeth may be disposed in a serial and/or overlapping configuration to provide a matrix of teeth.

In some embodiments, extension 28 includes an end, such as, for example, a flange 60 configured for plastic deformation to conform to vertebral tissue. In some embodiments, flange 60 is malleable and can be deformed, shaped and/or crimped to conform to vertebral tissue prior to implantation or in situ. In some embodiments, flange 60 can extend from extension 28 at various angular orientations, such as, for example, acute, obtuse and in a range of 0-360 degrees. In some embodiments, flange 60 can extend from extension 28 in a perpendicular, transverse, substantially aligned, twisted or helical orientation. In some embodiments, all or a selected width and/or length of extension 28 is configured for plastic deformation to conform to vertebral tissue, as described herein.

End 20 includes a portion, such as, for example, a transverse extension 70 that extends from portion 22 at an angular orientation. In some embodiments, extension 70 includes an undulating configuration, which comprises at least a portion of a gullwing configuration of spinal implant 12. In some embodiments, the undulating configuration of extension 70 and/or the gullwing configuration of spinal implant 12 facilitate manipulation thereof for engagement with anatomy, as described herein.

Extension 70 includes a fixation surface, such as, for example, surface 70a oriented to face and/or engage vertebral tissue, such as, for example, a lamina. In some embodiments, all or only a portion of extension 70 is engageable with a cut surface of tissue, as described herein. In some embodiments, surface 70a is roughened to facilitate engagement with tissue and provides an initial provisional fixation with tissue. In some embodiments, surface 70a includes teeth and/or rails to facilitate fixation with tissue. In some embodiments, surface 70a is smooth, porous, textured, rough, semi-porous, dimpled and/or polished.

In some embodiments, extension 70 can comprise a portion of spinal implant 12 that abuts and/or engages a separated surface of an anterior facing portion of vertebral tissue, as described herein. In some embodiments, extension 70 can extend from portion 22 at various angular orientations, such as, for example, acute, obtuse and in a range of 0-360 degrees. In some embodiments, extension 70 can extend from portion 22 in a perpendicular, transverse, substantially aligned, twisted or helical orientation.

Extension 70 includes an inner surface 72 that defines a cavity, such as, for example, an opening 74 configured to receive a bone screw 120. Extension 70 includes an inner surface 75 that defines a cavity, such as, for example, an opening 76 configured to receive a bone screw 120. Bone screw 120 attaches extension 70 and spinal implant 12 with vertebral tissue, as described herein. In some embodiments, extension 70 may include one or a plurality of cavities configured for disposal of a bone fastener.

In some embodiments, inner surface 75 defines an elongated cavity, which includes openings 76a, 76b to selectively orient bone screw 120 for penetrating vertebral tissue, as shown in FIGS. 3 and 4. In some embodiments, openings 76a, 76b communicate and are overlapping to provide adjustability of bone screw 120 for selectively orienting bone screw 120 for penetrating vertebral tissue. In some embodiments, openings 76a, 76b are spaced and do not overlap to provide adjustability of bone screw 120 for selectively orienting bone screw 120 for penetrating vertebral tissue. In some embodiments, the elongated cavity includes a circular opening 76a that defines a center axis and a circular opening 76b that defines a center axis. In some embodiments, the elongated cavity can include one or a plurality of openings, which may be disposed in linear alignment, series, an arc, undulating, offset, staggered, uniform, non-uniform, angled, cluster, random and/or cloverleaf configuration. In some embodiments, the center axes are relatively disposed in a parallel or transverse orientation. In some embodiments, openings 76a, 76b comprise a figure eight configuration such that opening 76a communicates with opening 76b to provide adjustability of bone screw 120 to selectively orient bone screw 120 for penetrating vertebral tissue. In some embodiments, an opening may have alternate configurations, such as, for example, oval, oblong, triangular, square, hexagonal, polygonal, irregular, uniform, non-uniform and/or tapered. In some embodiments, opening 74 and/or opening 76 is configured to orient bone screw 120 along a transverse axis of the lamina. In some embodiments, opening 74 and/or opening 76 is configured to orient bone screw 120 along a longitudinal axis of the lamina.

In some embodiments, intermediate portion 22 includes an inner surface 77 that defines a cavity, such as, for example, an opening 79 that extends along an axis X. In some embodiments, opening 79 is configured to provide an anchoring surface for spinal implant 12 with tissue. In some embodiments, opening 79 provides an anchoring surface to facilitate reconnecting of tissue, for example, to close an incision adjacent a surgical site. In some embodiments, opening 79 is configured to provide an attachment surface for a surgical delivery instrument, as described herein, to facilitate placement of spinal implant 12. In some embodiments, opening 79 may have alternate configurations, such as, for example, oval, oblong, triangular, square, hexagonal, polygonal, irregular, uniform, non-uniform and/or tapered. In some embodiments, intermediate portion 22 includes an anchoring surface or an attachment surface, as described above, for example, a detent, cavity, flange, clip, hook, ring or mating element, which can be connected, attached and/or manipulated by a practitioner and/or a surgical instrument. In some embodiments, a surface 81 of intermediate portion 22 includes a beveled edge 83 that defines a first section of opening 78 and another surface 85 of intermediate portion 22 includes a beveled edge 87 that defines a second section of opening 78, as shown in FIG. 2.

Extension 70 includes an outer surface 80, as shown in FIGS. 1 and 2. Outer surface 80 extends between an end 82 and an end 84. Outer surface 80 includes a mating element, such as, for example, a ridge 86. Ridge 86 is configured for engagement with surgical delivery instrument I, as described herein. Ridge 86 includes a surface, such as, for example, a ramp 88 and a surface, such as, for example, a ramp 90. Ramps 88, 90 are oriented to define an apex 92. Ramp 88, ramp 90 and/or apex 92 are configured as a grip surface to resist and/or prevent surgical delivery instrument I from disengagement and/or slipping from spinal implant 12 to resist and/or undesired engagement and/or damage to adjacent.

Ramps 88, 90 define end surfaces 96, 98. Surfaces 96, 98 are configured to facilitate alignment and engagement of surgical delivery instrument I with spinal implant 12, as described herein. In some embodiments, ridge 86 extends in a transverse orientation relative to ends 82, 84. In some embodiments, ridge 86 extends a distance between ends 82, 84. In some embodiments, the mating element includes a tooth disposed transversely along surface 80. In some embodiments, the mating element includes a plurality of teeth. In some embodiments, one or more teeth may have various configurations, for example, parallel, converging, diverging, irregular, tapered, offset, staggered, uniform and non-uniform. In some embodiments, the teeth may be disposed in a serial and/or overlapping configuration to provide a matrix of teeth.

In some embodiments, extension 70 includes an end, such as, for example, a flange 100 configured for plastic deformation to conform to vertebral tissue. In some embodiments, flange 100 is malleable and can be deformed, shaped and/or crimped to conform to vertebral tissue prior to implantation or in situ. In some embodiments, flange 100 can extend from extension 70 at various angular orientations, such as, for example, acute, obtuse and in a range of 0-360 degrees. In some embodiments, flange 100 can extend from extension 70 in a perpendicular, transverse, substantially aligned, twisted or helical orientation. In some embodiments, all or a selected width and/or length of extension 70 is configured for plastic deformation to conform to vertebral tissue, as described herein.

In some embodiments, all or only a portion of plate 14 is fabricated from a work hardenable material such that deformation of flange 60 and/or flange 100 stiffens extensions 28, 70. In some embodiments, extensions 28, 70 are monolithically formed with plate 14. In some embodiments, extensions 28, 70 are separate and attachable with plate 14 in situ or prior to implantation. In some embodiments, flanges 60, 100 are monolithically formed with extensions 28, 70. In some embodiments, flanges 60, 100 are separate and attachable to extensions 28, 70 in situ or prior to implantation.

In some embodiments, spinal implant 12 includes a cavity configured for disposal of bone growth promoting material. In some embodiments, the bone growth promoting material can include bone graft, allograft, xenograft, autograft, bone paste, bone chips, Skelite®, BMP and/or a titanium mesh material, such as, for example, Trabeculite™ available from Tecomet, Wilmington, Mass. In some embodiments, the cavity may include one or more agents, as described herein. In some embodiments, extensions 28, 70 may have a solid configuration. In some embodiments, extensions 28, 70 include an outer surface having perforations that communicate with bone growth promoting material disposed within the cavity.

Figure 7:
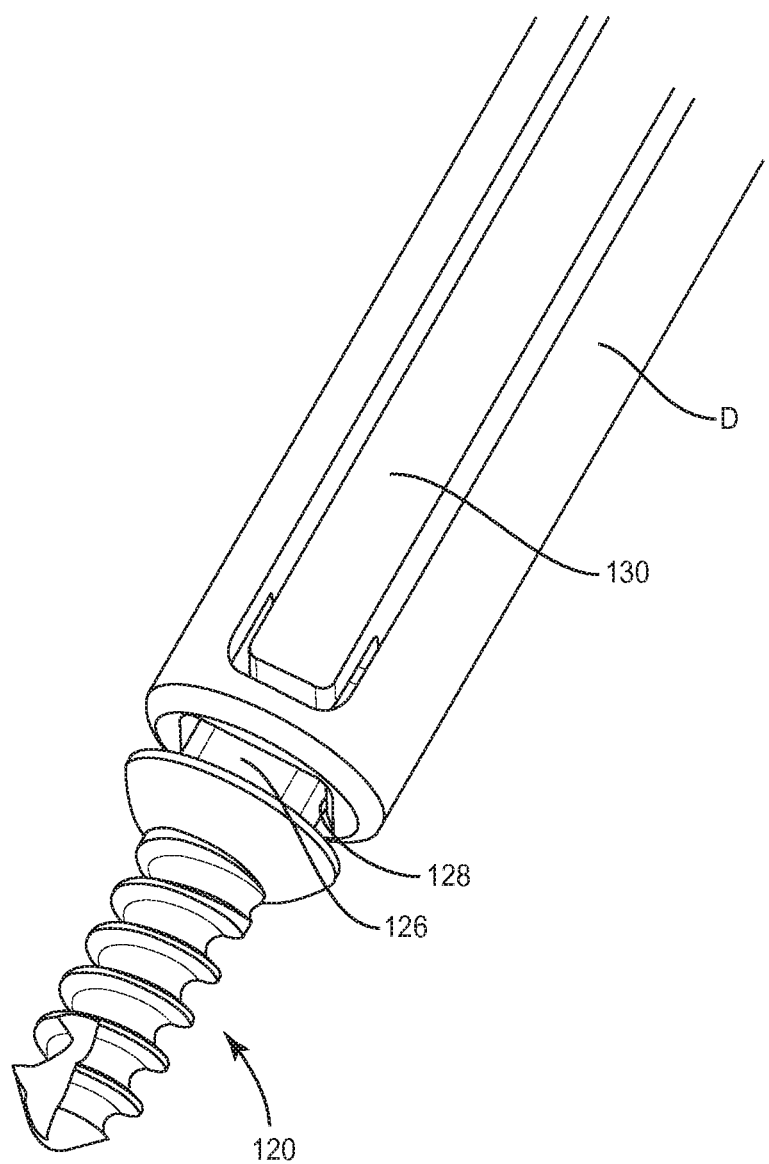
FIG. 7 is a break away perspective view of components of one embodiment of a system in accordance with the principles of the present disclosure.
Figure 8:
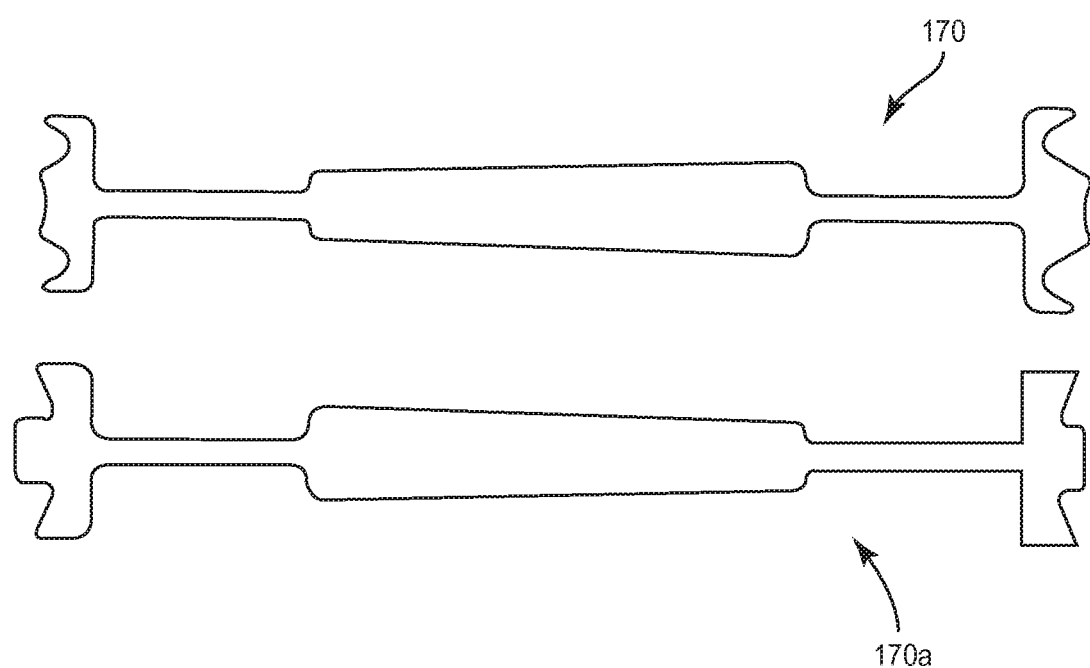
FIG. 8 is a plan view of components of one embodiment of a system in accordance with the principles of the present disclosure.

Bone screw 120 includes a portion, such as, for example, a head 122 and a portion, such as, for example a shaft 124, as shown in FIG. 5. Head 122 includes a tool engaging portion, such as, for example, a male mating portion 126. Male mating portion 126 is configured for engagement with a surgical driver D, as shown in FIG. 7. Male mating portion 126 includes a substantially square configuration. Surgical driver D includes a female mating portion 128 configured for mating engagement with male mating portion 126. Engagement of male mating portion 126 with female mating portion 128 resists and/or prevents disengagement from surgical driver D. In some embodiments, surgical driver D includes a flange 130 configured to facilitate connection of surgical driver D with bone screw 120. In some embodiments, flange 130 is resiliently biased inwardly to capture male mating portion 126 with female mating portion 128.

Shaft 124 includes an end 132 that forms a section, such as, for example, a neck 134 with head 122. Neck 134 is disposed adjacent head 122. Neck 134 is configured for disposal in a nested configuration such that head 122 is disposed with a countersunk portion of opening 32 and/or opening 34. Shaft 124 includes an outer surface 136 having a thread 138. Thread 138 extends along a length of shaft 124. In some embodiments, thread 138 is continuous along surface 136. In some embodiments, thread 138 may include a single thread turn or a plurality of discrete threads. In some embodiments, other penetrating elements may be located on shaft 124, such as, for example, a nail configuration, barbs, expanding elements, raised elements, ribs, and/or spikes to facilitate engagement of shaft 124 with tissue. In some embodiments, thread 138 may be self-tapping or intermittent. In some embodiments, shaft 124 is configured having various widths to facilitate engagement with tissue, such as, for example, bone screw 120, 120a, as shown in FIGS. 5 and 6.

In some embodiments, bone screw 120 can includes a selected diameter and or a selected length. In some embodiments, the diameter is selected based on a width of a vertebral level to maximize the diameter while maintaining the structural integrity of bone screw 120 when engaged with tissue, as shown in FIG. 6. In some embodiments, the length of bone screw 120 is determined based on a patient anatomy, such as, for example, a length of a vertebral level. In some cases, the length of a vertebral level may vary between male and female patients.

Figure 12:
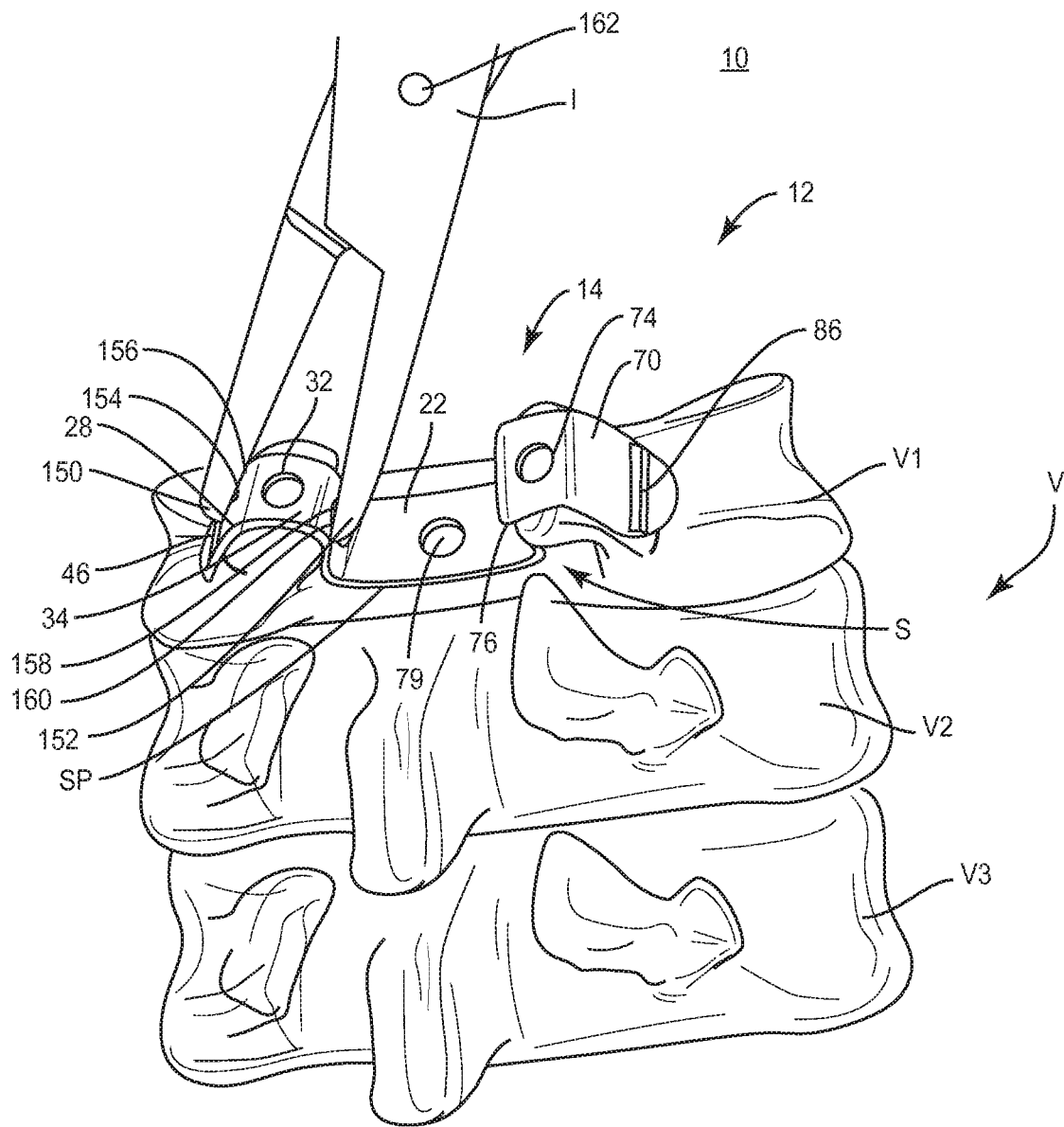
FIG. 12 is a perspective view of components of one embodiment of a system in accordance with the principles of the present disclosure disposed with vertebrae.

Surgical delivery instrument I, as shown in FIG. 12, is configured to facilitate manipulation, introduction, delivery and/or positioning of spinal implant 12 with tissue. Surgical delivery instrument I comprises a scissor and/or plier configuration that includes an arm having a tip 150 and an arm having a tip 152. Tips 150, 152 are connected via a pivot 162. Pivot 162 is configured to facilitate rotation of tip 150 relative to tip 152. Tips 150, 152 extend from the arms that are connected to portions of a handle for operation.

Tip 150 includes a mating element, such as, for example, a surface 154 that defines a cavity 156. Cavity 156 is configured for disposal of ridge 46 and/or ridge 86. Tip 152 includes a mating element, such as, for example, a surface 158 that defines a cavity 160. Cavity 160 is configured for disposal of ridge 46 and/or ridge 86.

Cavities 156, 160 align with ridges 46, 86 to facilitate connection of surgical delivery instrument I with extension 28 and/or extension 70 such that ridges 46, 86 are disposed therein. Surfaces 154, 158 engage ridges 46, 86 to grip plate 14 and resist and/or prevent surgical delivery instrument I from disengagement and/or slipping from plate 14 to resist and/or prevent undesired engagement and/or damage to adjacent tissue. In some embodiments, surfaces 154, 158 include protrusions, such as, for example, teeth configured to facilitate gripping of spinal implant 12. In some embodiments, tips 150, 152 include a transverse or curved configuration. In some embodiments, tips 150, 152 include a straight or linear configuration.

Surgical delivery instrument I engages extension 28 and/or extension 70 to facilitate implantation of spinal implant 12. Engagement of ridge 46 and/or ridge 86 with cavity 156 and/or cavity 160 resists and/or prevents surgical delivery instrument I from disengaging from spinal implant 12 to resist and/or prevent undesired engagement and/or damage to tissue. In some embodiments, tips 150, 152 are relatively rotated to capture spinal implant 12 therebetween to facilitate delivery to a surgical site. Compression of tips 150, 152 applies a force to extension 28 and/or extension 70. Compression of tips 150, 152 causes extensions 28, 70 to deform and/or crimp spinal implant 12 into a mating engagement with tissue.

Figure 13:
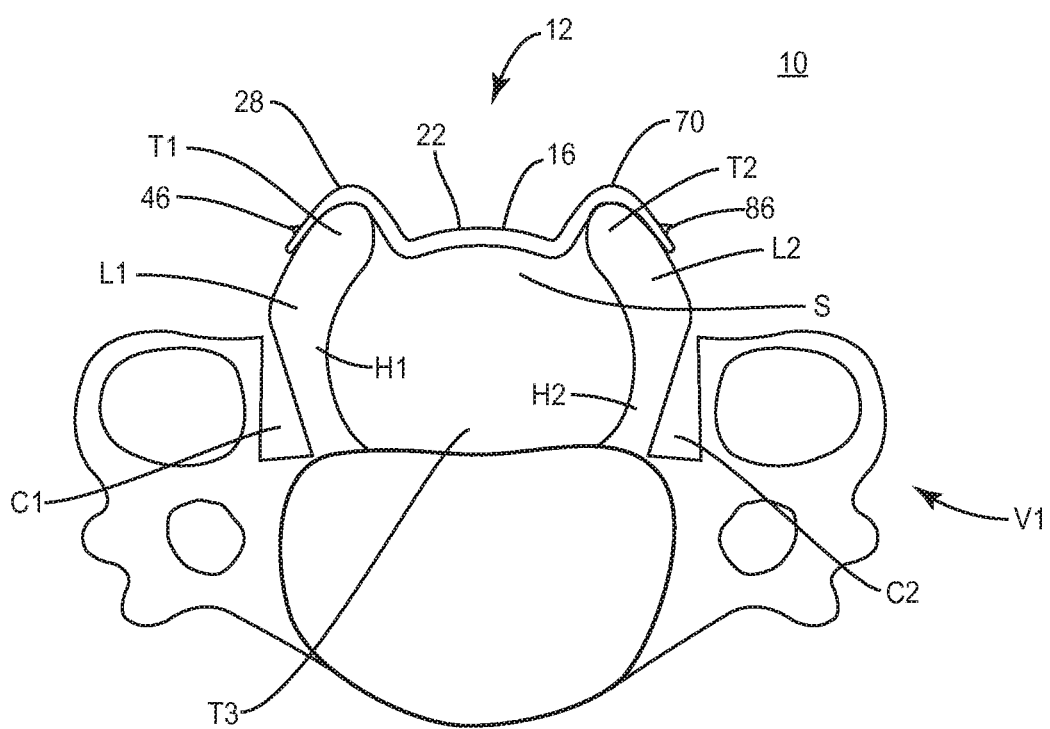
FIG. 13 is an axial view of components of one embodiment of a system in accordance with the principles of the present disclosure disposed with vertebrae.

In operation, as shown in FIGS. 12 and 13, spinal implant system 10, similar to the systems and methods described herein, is employed with a surgical procedure, such as, for example, a laminoplasty treatment of a spine of a patient including vertebrae V. Spinal implant system 10 may also be employed with other surgical procedures, such as, for example, discectomy, laminotomy, laminectomy, nerve root retraction, foramenotomy, facetectomy, decompression, and spinal, nucleus or disc replacement. For example, vertebral levels V1, V2 and V3 of vertebrae V can be removed, cut and/or weakened to open access and/or communication with a spinal canal T3 and/or spinal canal tissue, to provide space for a spinal cord. In some embodiments, spinal implant system 10 stabilizes vertebral levels V1, V2 and V3 for treatment and healing.

In some embodiments, to treat the affected section of vertebrae V, a medical practitioner obtains access to a surgical site including posterior elements of vertebrae V in any appropriate manner, such as through incision and retraction of tissues. Spinal implant system 10, similar to the systems and methods described herein, is employed with a surgical procedure, such as, for example, a laminoplasty treatment of a spine of a patient including vertebrae V. A cutting instrument (not shown) is employed to engage a spinous process (not shown-removed) of vertebral level V1. The spinous process is removed with the cutting instrument to form a cavity, gap or space S between lamina L1 and lamina L2.

A relief C1 is cut down a medial cortical layer of lamina L1 to create a bone hinge H1. A relief C2 is cut down the medial cortical layer of lamina L2 to create a bone hinge H2. In some embodiments, reliefs C1, C2 can include a groove, gutter or trough, and be formed using a high-speed burr drill. In some embodiments, reliefs C1, C2 have a depth of approximately 3 to 4 millimeters and a width of approximately 3 millimeters. In some embodiments, the associated ligamentum flavum, capsule, and/or veins adjacent vertebral level V1 can be separated to allow outward rotation of the separated laminae L1, L2.

In some embodiments, trial implants, such as, for example, trials 170, 170a, as shown in FIG. 7, are utilized to determine a selected size and/or configuration of spinal implant 12. In some embodiments, trials 170, 170a are configured with two ends each that are configured with a different size, such as, for example, a smaller end and a larger end. In some embodiments, trials 170, 170a include a tapered handle configured to indicate the smaller end and the larger end. In some embodiments, trials 170, 170a are manufactured from titanium. In some embodiments, trials 170, 170a are color coded to indicate dimension and configuration for selecting a spinal implant. In some embodiments, one of trials 170, 170a is delivered and used to determine a selected size and/or configuration of plate 14.

Surgical delivery instrument I is engaged with spinal implant 12, as shown in FIG. 12, to facilitate delivery to a surgical site. Surgical delivery instrument I is disposed adjacent extension 28 and tips 150, 152 are relatively rotated about pivot 162. Cavity 156 is aligned with ridge 46 such that ridge 46 is disposed in cavity 156 to facilitate connection of surgical delivery instrument I with extension 28 to capture plate 14. Surface 154 engages ridge 46 to grip plate 14 and resist and/or prevent surgical delivery instrument I from disengagement and/or slipping from plate 14 to resist and/or prevent undesired engagement and/or damage to adjacent tissue. Tip 152 engages an opposing portion of extension 28 such that tips 150, 152 apply a compression force to extension 28 about tissue, as described herein.

Similar to that described above, surgical delivery instrument I is disposed adjacent extension 70 and tips 150, 152 are relatively rotated about pivot 162. Cavity 160 is aligned with ridge 86 such that ridge 86 is disposed in cavity 160 to facilitate connection of surgical delivery instrument I with extension 70 to capture plate 14. Surface 158 engages ridge 86 to grip plate 14 and resist and/or prevent surgical delivery instrument I from disengagement and/or slipping from plate 14 to resist and/or prevent undesired engagement and/or damage to adjacent tissue. Tip 150 engages an opposing portion of extension 70 such that tips 150, 152 apply a compression force to extension 70 about tissue, as described herein.

Plate 14 is positioned with space S. Extensions 28, 70 are disposed about lamina L1 and lamina L2, as described herein, for engagement and/or fixation with vertebral tissue T1, T2. Compression of tips 150, 152 applies a force to extension 28 and/or extension 70 to deform and/or crimp plate 14 into engagement with tissue, such as, for example, extension 28 is positioned with tissue T1 of lamina L1 and extension 70 is positioned with tissue T2 of lamina L2. Extension 28 is manipulated for deformation, as described herein, about lamina L1 of vertebral level V1 for engagement and/or fixation with tissue T1 of vertebral level V1. Extension 70 is manipulated for deformation, as described herein, about lamina L2 of vertebral level V1 for engagement and/or fixation with tissue T2 of vertebral level V1.

In some embodiments, plate 14 is provided with bone growth promoting material and/or an agent, as described herein, to provide stabilization and decompression. Extensions 28, 70 are fastened with vertebral level V1, as described herein. Surfaces 28a, 70a are roughened and provide a provisional fixation of plate 14 to allow for alignment of screws 120. A pilot hole or the like is formed in tissue T1 and extension 28 is disposed such that opening 32 is aligned with the pilot hole in tissue T1. Screw 120 is disposed with opening 32 and inserted, drilled or otherwise fixed to tissue T1 to attach extension 28 with lamina L1. A pilot hole or the like is formed in tissue T2 and extension 70 is disposed such that opening 74 is aligned with the pilot hole in tissue T2. Screw 120 is disposed with opening 74 and inserted, drilled or otherwise fixed to tissue T2 to attach extension 70 with lamina L2.

A pilot hole or the like is formed in tissue T1 and extension 28 is disposed such that opening 34 is aligned with the pilot hole in tissue T1. Screw 120 is disposed with opening 34 and inserted, drilled or otherwise fixed to tissue T1 to attach extension 28 with lamina L1. A pilot hole or the like is formed in tissue T2 and extension 70 is disposed such that opening 76 is aligned with the pilot hole in tissue T2. Screw 120 is disposed with opening 76 and inserted, drilled or otherwise fixed to tissue T2 to attach extension 70 with lamina L2.

Figure 9:
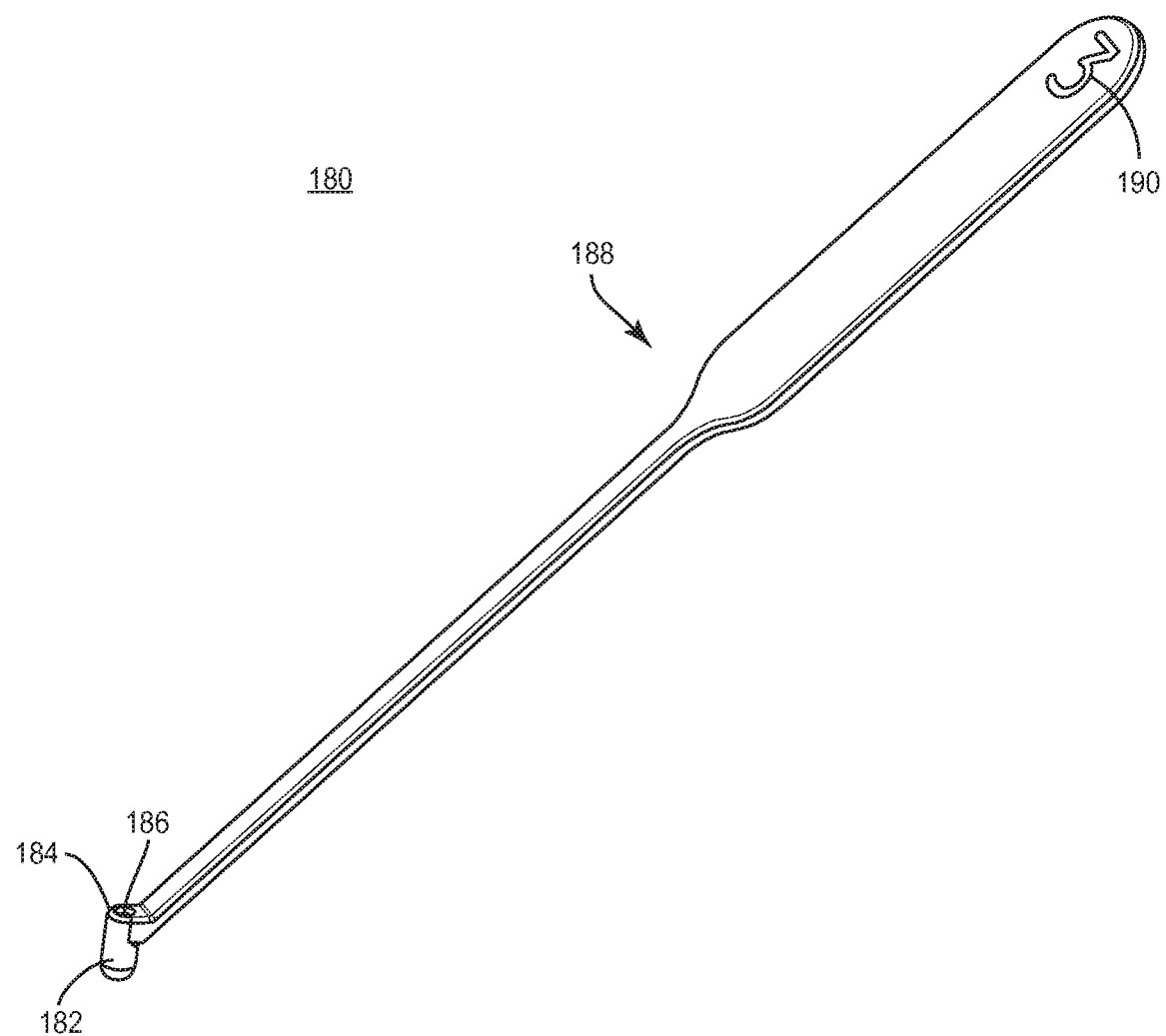
FIG. 9 is a perspective view of components of one embodiment of a system in accordance with the principles of the present disclosure.

In some embodiments, as shown in FIG. 9, spinal implant system 10 includes a surgical instrument, such as, for example, a surgical drill guide 180 that is employed with a surgical procedure, as described herein, to form one or more cavities, pilot holes or the like in tissue. Drill guide 180 can be employed with one or a plurality of surgical instruments including wires, awls, taps, drills and/or drivers in connection with delivery, orientation and/or fixation of plate 14 with tissue, as described herein. Drill guide 180 includes a housing 182 having a surface 184 that defines a passageway 186. Passageway 186 is configured for disposal of one or a plurality of the surgical instruments. Surface 184 and/or passageway 186 guide, align and/or direct the surgical instruments to form one or more cavities, pilot holes or the like in tissue at a surgical site. In some embodiments, housing 182 is disposed within one or more of the openings of plate 14 to guide, align and/or direct the surgical instruments to form one or more cavities, pilot holes or the like in tissue at a surgical site. In some embodiments, drill guide 180 is connected with plate 14 for delivering plate 14 to a surgical site.

In some embodiments, housing 182 includes a uniform cylindrical cross section configuration and a uniform dimension. In some embodiments, housing 182 may have alternate cross section configurations, such as, for example, oval, oblong, triangular, rectangular, square and/or polygonal. In some embodiments, surface 184 has various surface configurations, such as, for example, rough, threaded for connection with surgical instruments, arcuate, undulating, porous, semi-porous, dimpled, polished and/or textured.

Drill guide 180 includes a handle 188 that extends from housing 182. Handle 188 includes indicia 190 that corresponds to a selected size and/or configuration of one or more cavities, pilot holes or the like to be formed in tissue at a surgical site, and/or a spinal implant, such as, for example, a selected bone screw to be disposed with the one or more cavities, pilot holes or the like. For example, indicia 190 includes a numerical reference "3" to indicate that housing 182 is configured and dimensioned to guide, align and/or direct a surgical instrument that forms a 3 mm pilot hole in tissue and/or corresponds to a 3 mm bone screw. In some embodiments, one or more components of drill guide 180 are color coded to indicate dimension and configuration of one or more cavities, pilot holes or the like to be formed in tissue, and/or spinal implants.

Figure 10:
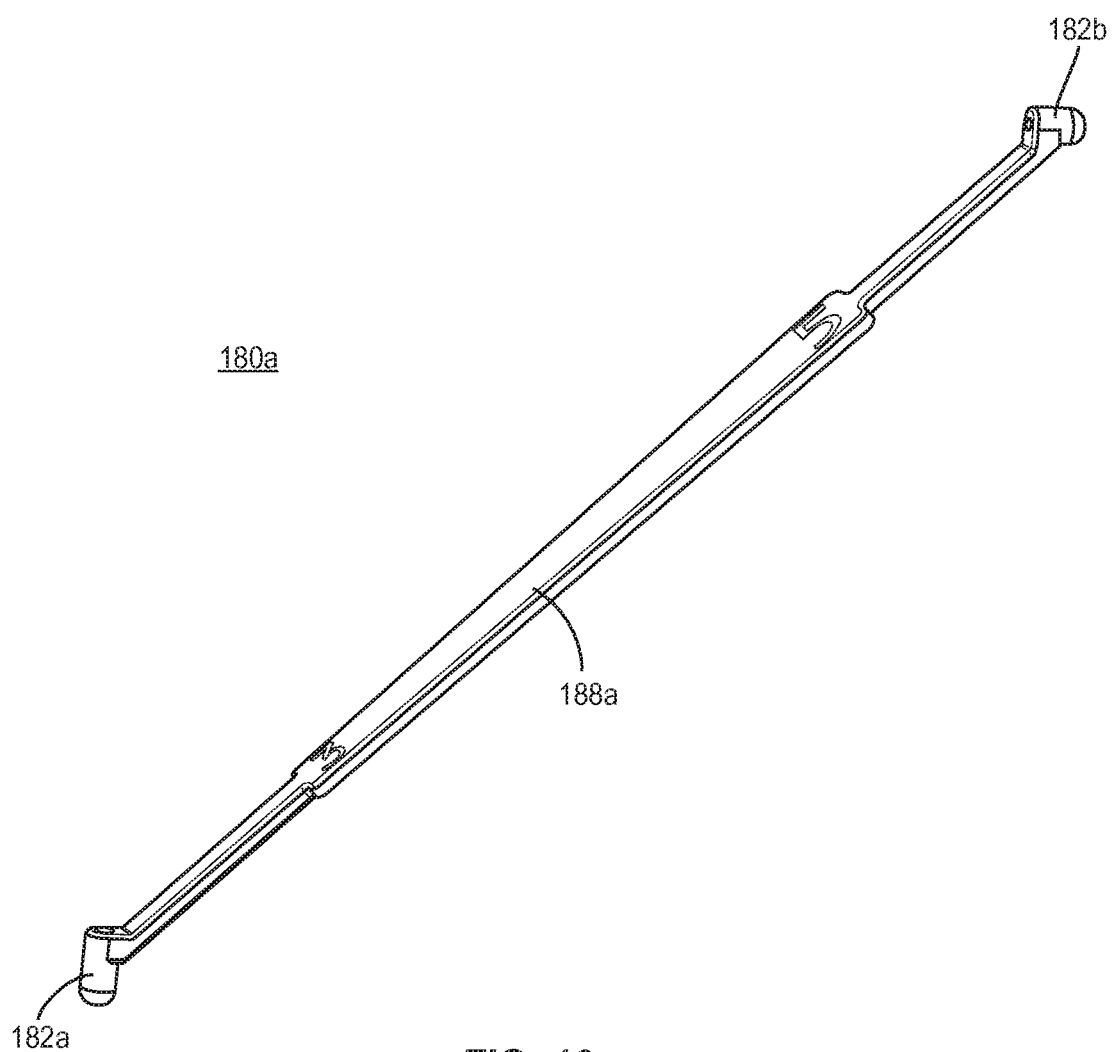
FIG. 10 is a perspective view of components of one embodiment of a system in accordance with the principles of the present disclosure.
Figure 11:
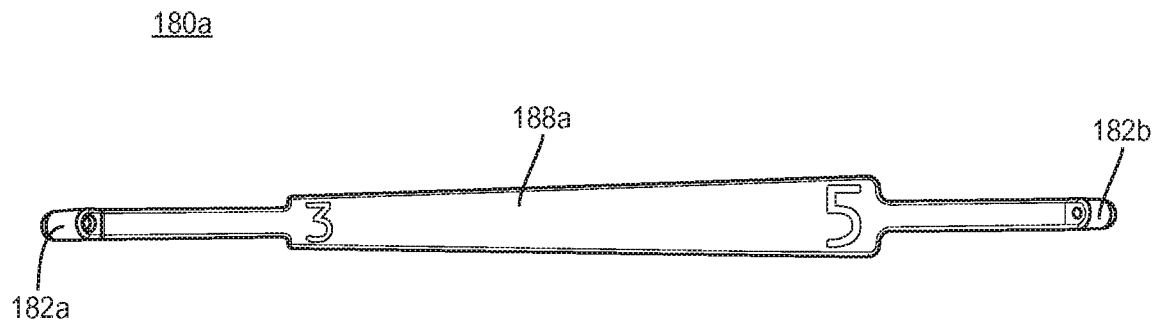
FIG. 11 is a side view of the components shown in FIG. 10.

In some embodiments, as shown in FIGS. 10 and 11, spinal implant system 10 includes a surgical drill guide 180a, similar to drill guide 180, having an intermediate handle 188a and housings 182a, 182b, similar to housing 182, being disposed at opposing ends of handle 188a. Housings 182a, 182b include indicia, similar to indicia 190, which corresponds to a selected size and/or configuration of one or more cavities, pilot holes or the like to be formed in tissue at a surgical site, and/or a spinal implant, such as, for example, a selected bone screw to be disposed with the one or more cavities, pilot holes or the like. For example, handle 188a is tapered to a larger housing 182b and tapered to a smaller housing 182a, to indicate a selected size and/or configuration of one or more cavities, pilot holes or the like and/or a spinal implant. In some embodiments, handle 188a includes indicia, for example, a numerical reference "3" to indicate that housing 182a is configured and dimensioned to guide, align and/or direct a surgical instrument that forms a 3 mm pilot hole in tissue and/or corresponds to a 3 mm bone screw. In some embodiments, handle 188a includes indicia, for example, a numerical reference "5" to indicate that housing 182b is configured and dimensioned to guide, align and/or direct a surgical instrument that forms a 5 mm pilot hole in tissue and/or corresponds to a 5 mm bone screw. In some embodiments, housings 182a, 182b are color coded to indicate dimension and configuration of one or more cavities, pilot holes or the like to be formed in tissue, and/or spinal implants.

In some embodiments, screw 120 is disposed with portions 34a, 34b, as shown in FIG. 3, inserted and adjusted for selective orientation with portions 34a, 34b for fixation with tissue T1 to attach extension 28 with lamina L1. In some embodiments, screw 120 is disposed with portions 76a, 76b, as shown in FIG. 3, inserted and adjusted for selective orientation with portions 76a, 76b for fixation with tissue T2 to attach extension 70 with lamina L2.

One or more of the components of spinal implant system 10 can be made of radiolucent materials such as polymers. Radiomarkers may be included for identification under x-ray, fluoroscopy, CT or other imaging techniques. In some embodiments, the use of surgical navigation, microsurgical and image guided technologies may be employed to access, view and repair spinal deterioration or damage, with the aid of spinal implant system 10. In some embodiments, spinal implant system 10 may include one or a plurality of spinal implants 12 for use with a single vertebral level or a plurality of vertebral levels.

In some embodiments, spinal implant system 10 includes an agent, which may be disposed, packed or layered within, on or about the components and/or surfaces of spinal implant 12. In some embodiments, the agent may include bone growth promoting material, such as, for example, bone graft to enhance fixation of the fixation elements with vertebrae. In some embodiments, the agent may include one or a plurality of therapeutic agents and/or pharmacological agents for release, including sustained release, to treat, for example, pain, inflammation and degeneration. Upon completion of the procedure, the non-implanted components, instruments and assemblies are removed and the incision(s) are closed.

Figure 14:
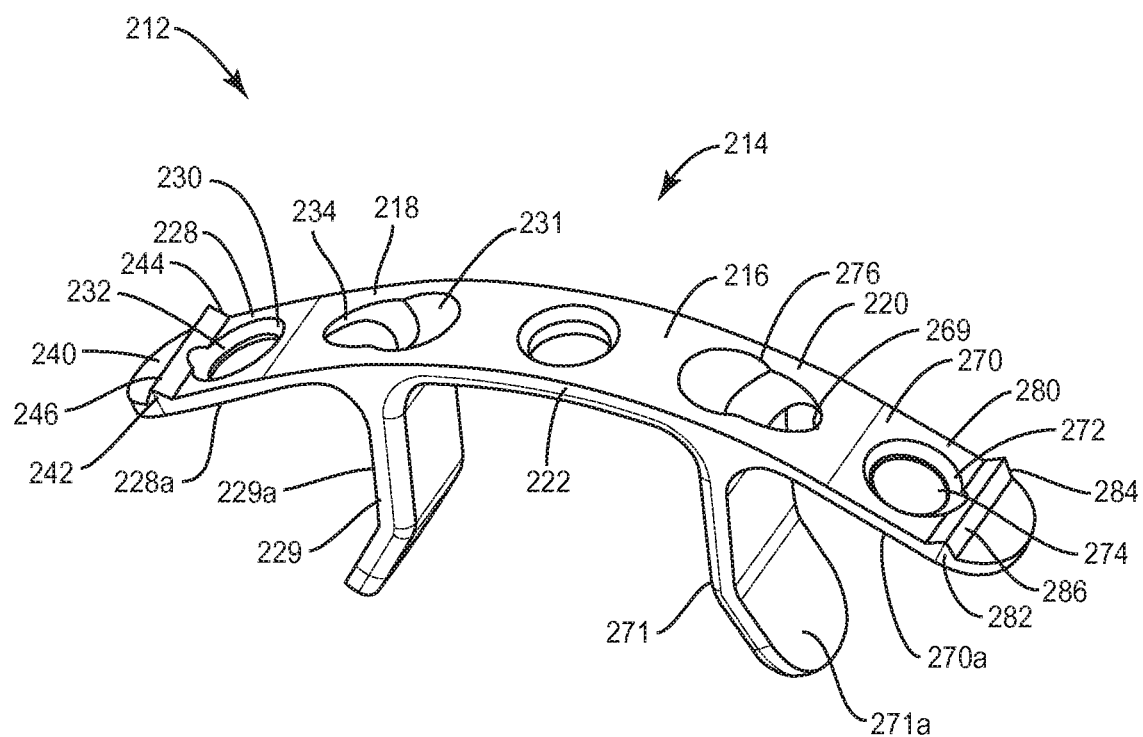
FIG. 14 is a perspective view of components of one embodiment of a system in accordance with the principles of the present disclosure.
Figure 15:
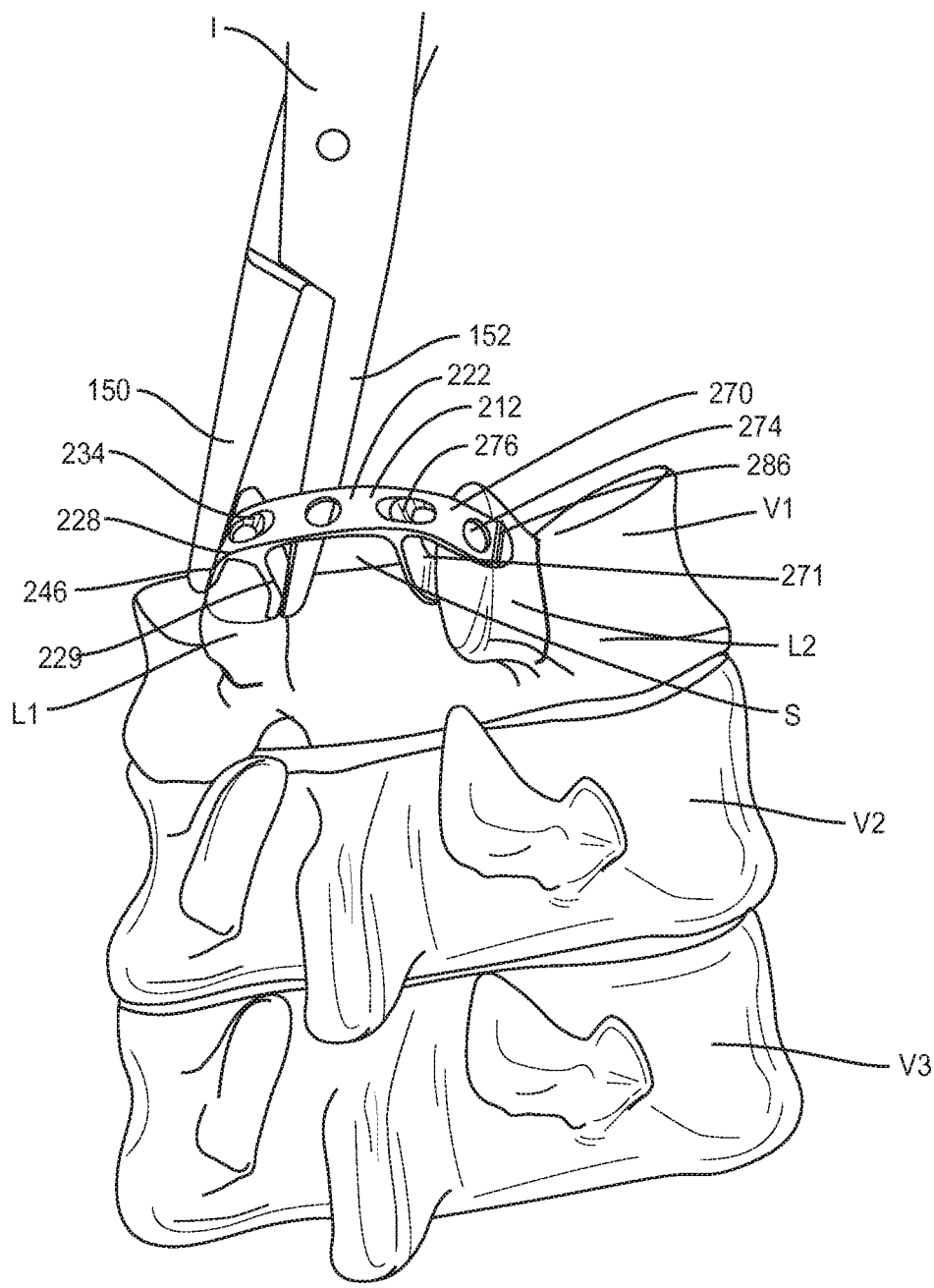
FIG. 15 is a perspective view of components of one embodiment of a system in accordance with the principles of the present disclosure disposed with vertebrae.
Figure 16:
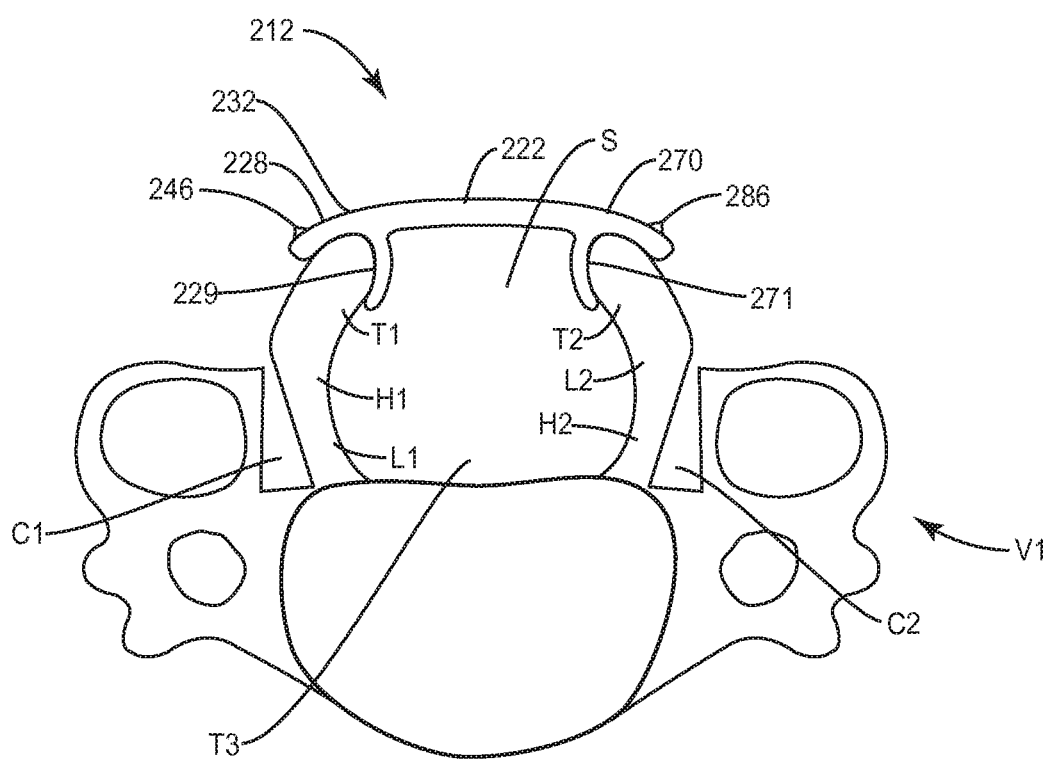
FIG. 16 is an axial view of components of one embodiment of a system in accordance with the principles of the present disclosure disposed with vertebrae.

In one embodiment, as shown in FIGS. 14-16, spinal implant system 10, similar to the systems and methods described above with regard to FIGS. 1-13, includes a spinal implant 212, similar to spinal implant 12 described herein, which is employed with a laminoplasty treatment configured for stabilizing one or more vertebral levels via attachment with a vertebral level V1, which has removed portions of vertebral tissue.

Spinal implant 212 includes a plate 214 having a tissue barrier 216. Tissue barrier 216 extends between an end 218 and an end 220, and includes a portion 222 disposed intermediate and/or therebetween. Tissue barrier 216 includes a wall having a substantially uniform, rectangular cross section. End 218 is spaced apart from end 220, and portion 222 has a non-planar face, such as, for example, an arcuate configuration including a curvature that is oriented adjacent tissue, such as, for example, a spinal canal.

End 218 includes a portion, such as, for example, a transverse extension 228 and a transverse extension 229. Extensions 228, 229 extend from portion 222 at an angular orientation. Extensions 228, 229 include a fixation surface, such as, for example, surfaces 228a, 229a that form a cavity oriented to face and/or engage lamina. In some embodiments, extensions 228, 229 are configured for plastic deformation to conform to vertebral tissue. In some embodiments, extensions 228, 229 are malleable and can be deformed, shaped and/or crimped to conform to vertebral tissue prior to implantation or in situ.

Extension 228 includes an inner surface 230 that defines a cavity, such as, for example, an opening 232 configured to receive a bone fastener, such as, for example, a bone screw 120, as discussed herein and shown in FIGS. 5 and 6. Bone screw 120 attaches extension 228 and spinal implant 212 with vertebral tissue, as described herein. In some embodiments, extension 228 may include one or a plurality of cavities configured for disposal of a bone fastener. In some embodiments, extension 228 includes an inner surface 231 having a countersunk portion that defines an angled opening 234 to provide for transverse and/or angled orientation of bone screw 120 to selectively orient bone screw 120 for penetrating vertebral tissue.

Extension 228 includes an outer surface 240. Outer surface 240 extends between an end 242 and an end 244. Outer surface 240 includes a mating element, such as, for example, a ridge 246, similar to ridge 46, described herein. Ridge 246 is configured for engagement with surgical delivery instrument I, as described herein.

End 220 includes a portion, such as, for example, a transverse extension 270 and a transverse extension 271. Extensions 270, 271 extend from portion 222 at an angular orientation. Extensions 270, 271 include a fixation surface, such as, for example, surfaces 270a, 271a that form a cavity oriented to face and/or engage lamina. In some embodiments, extensions 270, 271 are configured for plastic deformation to conform to vertebral tissue. In some embodiments, extensions 270, 271 are malleable and can be deformed, shaped and/or crimped to conform to vertebral tissue prior to implant or in situ.

Extension 270 includes an inner surface 272 that defines a cavity, such as, for example, an opening 274 configured to receive a bone screw 120, as described herein. Bone screw 120 attaches extension 270 and spinal implant 212 with vertebral tissue, as described herein. In some embodiments, extension 270 includes an inner surface 269 having a countersunk portion that defines an angled opening 276 to provide for transverse and/or angled orientation of bone screw 120 to selectively orient bone screw 120 for penetrating vertebral tissue.

Extension 270 includes an outer surface 280. Outer surface 280 extends between an end 282 and an end 284. Outer surface 280 includes a mating element, such as, for example, a ridge 286, similar to ridge 86 described herein.

In operation, as shown in FIGS. 15 and 16, spinal implant system 10, similar to the systems and methods described herein, is employed with a surgical procedure, such as, for example, a laminoplasty treatment of a spine of a patient including vertebrae V. A cutting instrument (not shown) is employed to engage a spinous process (not shown-removed) of vertebral level V1. The spinous process is removed with the cutting instrument to form a cavity, gap or space S between lamina L1 and lamina L2.

A relief C1 is cut down a medial cortical layer of lamina L1 to create a bone hinge H1. A relief C2 is cut down the medial cortical layer of lamina L2 to create a bone hinge H2. In some embodiments, reliefs C1, C2 can include a groove, gutter or trough, and be formed using a high-speed burr drill. In some embodiments, reliefs C1, C2 have a depth of approximately 3 to 4 millimeters and a width of approximately 3 millimeters. In some embodiments, the associated ligamentum flavum, capsule, and/or veins adjacent vertebral level V1 can be separated to allow outward rotation of the separated laminae L1, L2.

Surgical delivery instrument I, as described herein, is engaged with spinal implant 212, as shown in FIG. 15, to facilitate delivery to a surgical site. Surgical delivery instrument I is disposed adjacent extension 228 and tips 150, 152 are relatively rotated about pivot 162. Cavity 156 is aligned with ridge 246 such that ridge 246 is disposed in cavity 156 to facilitate connection of surgical delivery instrument I with extension 228 to capture plate 214. Surface 154 engages ridge 246 to grip plate 214 and resist and/or prevent surgical delivery instrument I from disengagement and/or slipping from plate 214 to resist and/or prevent undesired engagement and/or damage to adjacent tissue. Tip 152 engages an opposing portion of extension 228 such that tips 150, 152 apply a compression force to extension 228 about tissue, as described herein.

Similar to that described above, surgical delivery instrument I is disposed adjacent extension 270 and tips 150, 152 are relatively rotated about pivot 162. Cavity 160 is aligned with ridge 286 such that ridge 286 is disposed in cavity 160 to facilitate connection of surgical delivery instrument I with extension 270 to capture plate 214. Surface 158 engages ridge 286 to grip plate 214 and resist and/or prevent surgical delivery instrument I from disengagement and/or slipping from plate 214 to resist and/or prevent undesired engagement and/or damage to adjacent tissue. Tip 150 engages an opposing portion of extension 270 such that tips 150, 152 apply a compression force to extension 270 about tissue, as described herein.

Extensions 228, 229 and extensions 270, 271 are positioned with lamina L1 and lamina L2, respectively. Lamina L1 is rotated outwardly about bone hinge H1 and lamina L2 is rotated outwardly about bone hinge H2 to enlarge the cross-sectional area of spinal canal T3. Plate 214 is positioned with space S between the separated surfaces of tissue T1, T2. Extensions 228, 229 are disposed with lamina L1 and extensions 270, 271 are disposed with lamina L2 to provide stabilization and decompression.

As described above, extensions 228, 229 are manipulated to deform about lamina L1 of vertebral level V1 for engagement and/or fixation with tissue T1 of vertebral level V1. Extensions 270, 271 are manipulated to deform about lamina L2 of vertebral level V1 for engagement and/or fixation with tissue T2 of vertebral level V1. In some embodiments, extensions 228, 229, 270, 271 and plate 214 can prevent the separated laminae from closing from an implant position toward an original, non-implant position. In some embodiments, extensions 228, 229, 270, 271 tightly abut the spaced apart laminae.

Surfaces 228a, 229a, 270a, 271a are roughened and provide a provisional fixation of spinal implant 212 to allow for alignment of screws 120. A pilot hole or the like is formed in tissue T1 and extension 228 is disposed such that opening 232 is aligned with the pilot hole in tissue T1. A screw 120 is disposed with opening 232 and inserted, drilled or otherwise fixed to tissue T1 to attach extension 228 with lamina L1. A pilot hole or the like is formed in tissue T2 and extension 270 is disposed such that opening 274 is aligned with the pilot hole in tissue T2. A screw 120 is disposed with opening 274 and inserted, drilled or otherwise fixed to tissue T2 to attach extension 270 with lamina L2.

A transverse and/or angled pilot hole or the like is formed in tissue T1 and extension 228 is disposed such that angled opening 234 is aligned with the pilot hole in tissue T1. A screw 120 is disposed with opening 234 and inserted, drilled or otherwise fixed to tissue T1 to attach extension 228 from a transverse orientation with lamina L1. A transverse and/or angled pilot hole or the like is formed in tissue T2 and extension 270 is disposed such that angled opening 276 is aligned with the pilot hole in tissue T2. A screw 120 is disposed with opening 276 and inserted, drilled or otherwise fixed to tissue T2 to attach extension 270 from a transverse orientation with lamina L2. Upon completion of the procedure, the non-implanted components, instruments and assemblies are removed and the incision(s) are closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
an intermediate portion including a first end and a second end, the intermediate portion including opposite inner and outer surfaces that each extend continuously from the first end to the second end, the intermediate portion including a first opening that extends through the inner and outer surfaces positioned between the first end and the second end, wherein an axis extends at least partially between the inner and outer surfaces from the first end to the second end;
a first portion including a second opening between opposite first and second ends of the first portion, the first end of the first portion extending in a transverse orientation from the first end of the intermediate portion, an end surface of the second end of the first portion being positioned along the axis, the first portion including an inner surface connectable with vertebral tissue adjacent a lamina; and
a second portion spaced from the first portion and extending in a transverse orientation from the second end, the second portion including an inner surface connectable with vertebral tissue adjacent a lamina, the second portion being monolithically formed with the intermediate portion and the first portion,
wherein the first portion includes a mating part extending outwardly from an outer surface of the first portion.

2. A spinal implant as recited in claim 1, wherein the mating part of the first portion includes at least one tooth.

3. A spinal implant as recited in claim 1, wherein the mating part of the first portion includes at least one ridge.

4. A spinal implant as recited in claim 1, wherein the mating part of the first portion includes a ridge disposed along the outer surface of the first portion, the ridge including first and second ramps oriented to define an apex.

5. A spinal implant as recited in claim 1, wherein the mating part of the first portion includes a grip surface to resist and/or prevent disengagement of a surgical instrument from the first portion.

6. A spinal implant as recited in claim 1, wherein the mating part of the first portion includes a first planar ramp and a second planar ramp, an interface between the first planar ramp and the second planar ramp defining an apex.

7. A spinal implant as recited in claim 1, wherein the intermediate portion defines a first height of the spinal implant and the first portion and the second portion each define a second height of the spinal implant, the first and second heights each extending substantially perpendicular to the axis, the second height being greater than the first height.

8. A spinal implant as recited in claim 7, wherein the first height is a maximum height of the intermediate portion and the second height is a maximum height of the first portion and a maximum height of the second portion.

9. A spinal implant as recited in claim 1, wherein at least one of the portions includes an elongated opening disposed to selectively orient a fastener for penetrating the vertebral tissue.

10. A spinal implant as recited in claim 1, wherein the inner surface of the intermediate portion includes a beveled edge that defines a first section of the first opening and the outer surface includes a beveled edge that defines a second portion of the first opening.

11. A spinal implant as recited in claim 1, wherein at least one of the portions includes an opening having a figure eight configuration.

12. A spinal implant as recited in claim 1, wherein at least one of the portions includes a plastically deformable extension.

13. A spinal implant as recited in claim 1, wherein:
a first outer surface of the spinal implant is concavely curved between the first end of the intermediate portion and the first end of the first portion and a second outer surface of the spinal implant is concavely curved between the second end of the intermediate portion and a first end of the second portion; and
a first inner surface of the spinal implant is convexly curved between the first end of the intermediate portion and the first end of the first portion and a second inner surface of the spinal implant is concavely curved between the second end of the intermediate portion and a first end of the second portion.

14. A spinal implant comprising:
a tissue barrier including a first end and a second end that is monolithically formed with the first end, the tissue barrier including opposite inner and outer surfaces that each extend continuously from the first end to the second end, the inner surface being concave from the first end to the second end, the tissue barrier including a first opening that extends through the inner and outer surfaces positioned between the first end and the second end, wherein an axis extends at least partially between the inner and outer surfaces from the first end to the second end,
a first deformable extension comprising a second opening between opposite first and second ends of the first extension, the first end of the first extension extending from the first end of the tissue barrier, an end surface of the second end of the first extension being positioned along the axis, the first extension including an inner surface connectable with vertebral tissue adjacent a lamina and an opposite outer surface having at least one ridge, the outer surface of the first extension being convexly curved from the first end of the first extension to the second end of the first extension;
and
a second deformable extension comprising a first end extending from the second end of the tissue barrier and an opposite second end, the second extension comprising an inner surface connectable with vertebral tissue adjacent a lamina and an opposite outer surface having at least one ridge, the outer surface of the second extension being convexly curved from the first end of the second extension to the second end of the second extension,
wherein the outer surfaces of the extensions are continuous with the outer surface of the tissue barrier.

15. A spinal implant system comprising:
a plate including an intermediate portion including a first end and a second end, the intermediate portion including opposite inner and outer surfaces that each extend continuously from the first end to the second end, the intermediate portion including a first opening that extends through the inner and outer surfaces positioned between the the first end and the second end, wherein an axis extends at least partially between the inner and outer surfaces from the first end to the second end, the plate including a first transverse extension comprising a second opening between opposite first and second ends of the first extension, the first end of the first extension extending from the first end of the intermediate portion, an end surface of the second end of the first extension being positioned along the axis, an outer surface of the first extension being convexly curved from the first end of the first extension to the second end of the first extension, the plate including a second transverse extension comprising a first end extending from the second end of the intermediate portion and an opposite second end, an outer surface of the second extension being convexly curved from the first end of the second extension to the second end of the second extension, the outer surfaces of the extensions each including a mating element, at least one of the extensions including an opening;
a surgical instrument engageable with the mating element; and
a fastener disposable with the opening.

16. A spinal implant as recited in claim 15, wherein the first extension includes a circular opening extending through a thickness of the first extension and the second extension includes a circular opening extending through a thickness of the second extension.

17. A spinal implant as recited in claim 15, wherein the outer surfaces of the extensions are continuous with the outer surface of the intermediate portion.

18. A spinal implant as recited in claim 15, wherein at least one of the extensions is plastically deformable via the surgical instrument.

* * * * *